United States Patent [19]

Cilento et al.

[11] Patent Number: 4,775,374
[45] Date of Patent: Oct. 4, 1988

[54] SKIN BARRIER FOR USE BY OSTOMATES

[75] Inventors: Rudolfo D. Cilento, North Brunswick; Edward C. Smith, Jr., Hamilton Township, Mercer County; Frank M. Freeman, Lawrenceville, all of N.J.

[73] Assignee: E. R. Squibb & Sons, Inc., Princeton, N.J.

[21] Appl. No.: 65,114

[22] Filed: Jun. 24, 1987

Related U.S. Application Data

[63] Continuation of Ser. No. 325,465, Nov. 27, 1981, abandoned.

[51] Int. Cl.4 .............................................. A61F 5/44
[52] U.S. Cl. ................................... 604/344; 604/338; 604/339
[58] Field of Search ................................ 604/332–345

[56] References Cited

U.S. PATENT DOCUMENTS

| 2,575,063 | 11/1951 | Mette | 128/283 |
|---|---|---|---|
| 3,121,021 | 2/1964 | Copeland | 117/122 |
| 3,339,546 | 9/1967 | Chen | 128/156 |
| 3,439,679 | 4/1969 | Doolittle | 128/283 |
| 3,736,934 | 6/1973 | Hennessy | 128/283 |
| 3,972,328 | 8/1976 | Chen | 128/156 |
| 4,192,785 | 3/1980 | Chen et al. | 128/283 |
| 4,213,458 | 7/1980 | Nolan et al. | 128/283 |
| 4,427,737 | 1/1984 | Cilento et al. | 428/315.7 |
| 4,460,363 | 7/1984 | Steer et al. | 604/336 |

FOREIGN PATENT DOCUMENTS

| 63898 | 11/1982 | European Pat. Off. |
| 839818 | 3/1960 | United Kingdom |
| 1571657 | 7/1980 | United Kingdom |
| 2064333 | 6/1981 | United Kingdom |
| 2115288 | 3/1983 | United Kingdom |

OTHER PUBLICATIONS

E. R. Squibb, Stomahesive Application Technique, Revised Jan. 1973, Oct. 1974, Jul. 1976.
Kodner, Clinical Symposia—Colostomy and Ileostomy, vol. 30, No. 5, pp. 30–32, (1978).
Geels et al., The Enterocutaneous Fistula..., Nursing, Apr. 1978, pp. 52–55.
Miller et al., Instructions for the Care of the Urinary Stoma, Cleveland Clinic Foundation, 1971, 1–21.
Mahoney, Guide to Ostomy Nursing Care, pp. 112–113, (1976).
Honesty, Essentials of Abdominal Ostomy Care, pp. 29–32, (1972).
Sparberg, Ileostomy Care, pp. 25–37, (1971).
Gill et al., Instructions for the Care of the Urinary Stoma, 1972, pp. 1–24.
Gill et al., Instructions for the Care of the Ileostomy Stoma, 1972, 1–23.
Gill et al., Ostomy Care, vol. 1, 1979, pp. 21–32.

Primary Examiner—C. Fred Rosenbaum
Assistant Examiner—Sharon Rose
Attorney, Agent, or Firm—Lawrence S. Levinson; Stephen B. Davis

[57] ABSTRACT

A composite skin barrier including a first adhesive component which fits around the stoma, a coupling element, and a second adhesive component which is flexible, light, and has a degree of porosity. The second adhesive component contacts the skin at a distance from the stoma.

9 Claims, 2 Drawing Sheets

SKIN BARRIER FOR USE BY OSTOMATES

This is a continuation of copending application Ser. No. 325,465 filed on Nov. 27, 1981 now abandoned.

BACKGROUND OF THE INVENTION

Major abdominal surgery for a number of diseases involving different parts of the gastro-intestinal and urinary tract can result in a patient being left with an abdominal stoma. The three most common types of abdominal stoma are the colostomy, the ileostomy, and the ileal conduit. In the case of an ileostomy, ileal conduit, and many colostomy operations, the patient is unable to control the passage of bodily waste material and must rely upon an appliance attached to their body to collect this material.

Numerous appliances have been proposed for this purpose. Most can be characterized as either a one-piece or a two-piece system. The one-piece appliance conventionally consists of a pouch having an opening in one sidewall for the stoma around which a plastic faceplate is permanently bonded. The faceplate includes an outer layer of adhesive material which is designed to affix the appliance directly to the body or to an intermediate skin barrier or sealing washer. The two-piece appliance conventionally consists of a mounting ring that is supported on the body by means of an elastic belt.

Recently, the two-piece appliance disclosed by Steer et al. in British Patent No. 1,571,657 and U.S. Ser. No. 881,274, now abandoned in favor of Ser. No. 394,659 filed on July 2, 1982, now U.S. Pat. No. 4,460,363, has achieved considerable commercial success. The Steer et al. appliance consists of a skin barrier having a projecting rib type coupling member affixed to its outer surface and a pouch with a channel shaped coupling member encircling the stoma opening in the pouch sidewall. The pouch can be securely attached to the skin barrier by snapping onto the rib. The skin barrier employed by Steer et al. is that described by Chen in U.S. Pat. No. 3,339,546 and includes an adhesive layer consisting of a mixture of gelatin, pectin, sodium carboxymethylcellulose, and polyisobutylene and an outer water insoluble polyethylene film to which the rib coupling member is affixed.

SUMMARY OF THE INVENTION

This invention is directed to a composite type skin barrier product which includes a coupling element to which a pouch can be easily and securely attached. This skin barrier has improved flexibility and is lighter and more comfortable on the body than those currently employed. As a result of its increased flexibility, the skin barrier provides a stronger bond with the skin and is not subject to cracking, creasing, or lifting as the anatomy underneath bends or stretches.

The composite skin barrier of this invention includes a first adhesive component which fits around the stoma, a coupling element, and a second adhesive component which is flexible, light, and has a degree of porosity or breathability.

In the preferred embodiment, the coupling element is permanently affixed to the top of the first adhesive component around the stomal opening and the second adhesive component overlaps a flange portion of the coupling element and any exposed top portion of the first adhesive component which is exterior to the coupling element.

In an alternative embodiment, the porous adhesive component is bonded to the top of the first adhesive component and the coupling element is affixed directly to the second adhesive component.

DETAILED DESCRIPTION

Figure 1:
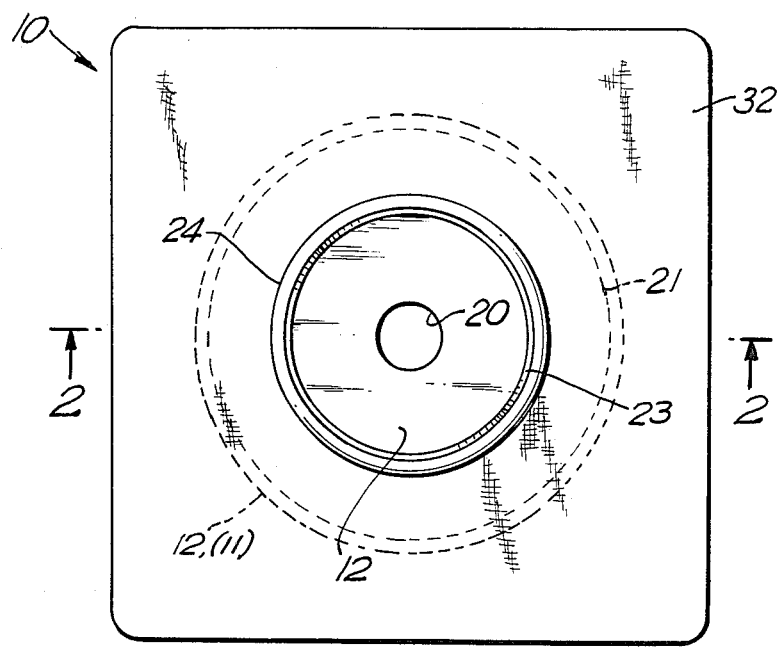
FIG. 1 is a top view of the skin barrier of this invention including the preferred coupling element.
Figure 2:
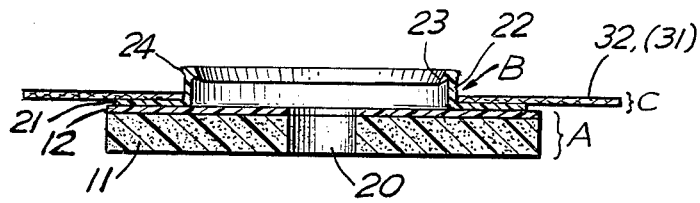
FIG. 2 is a front view taken along line 2—2 of FIG. 1.
Figure 3:
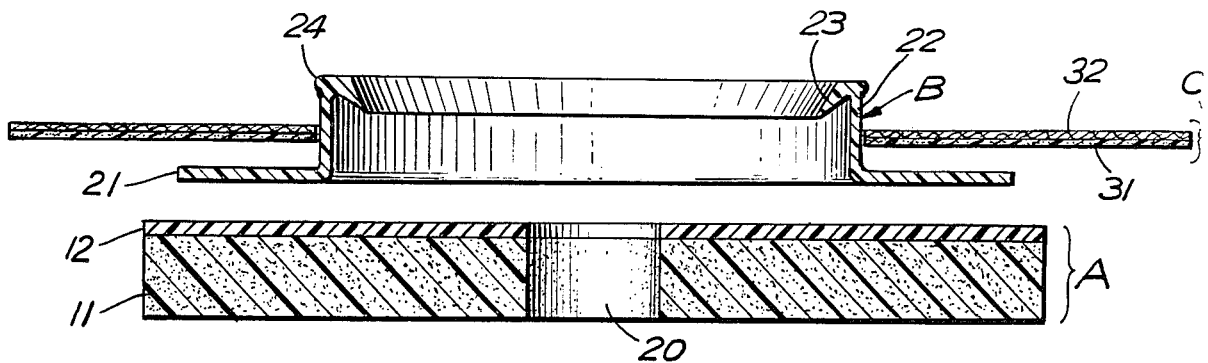
FIG. 3 is an exploded view of the composite skin barrier as shown in FIG. 2 in greatly enlarged detail.

Referring to FIGS. 1-3 in more particular detail, the composite skin barrier 10 consists of three components. Component A rncludes an adhesive layer 11 and an outer polymeric film 12 and is shown with a centrally located opening or starter hole 20 which can be enlarged to fit snugly around a stoma. Component B is a coupling element which is permanently affixed to outer polymeric film 12. Component C is a flexible microporous tape having an adhesive layer 31 that overlaps flange portion 21 of the coupling element and any of polymeric film 12 not affixed to flange 21. Outer surface 32 of the microporous tape is a porous backing layer. In use, adhesive surface 31 is pressed onto the body a distance from the stoma and aids adhesive layer 11 in maintaining the skin barrier in place. Component A may extend exactly to the end of flange 21 of component B or slightly beyond as shown in FIGS. 1 to 3.

The adhesive layer 11 is a homogeneous blend of one or more pressure sensitive adhesive materials having intimately dispersed therein one or more water soluble hydrocolloid gums. Optionally, one or more thermoplastic elastomers can be included with the pressure sensitive adhesive materials and one or more water swellable or inert cohesive strengthening agents can be included with the hydrocolloid gums.

Suitable pressure sensitive adhesive materials for inclusion in adhesive layer 11 are various natural or synthetic viscous or elastomeric substances such as natural rubber, silicone rubber, acrylonitrile rubber, polyurethane rubber, polyisobutylene, etc., either possessing dry tack by themselves or developing such tack upon the addition of a plasticizer. Low molecular weight polyisobutylenes having a viscosity average molecular weight of from about 36,000 to about 58,000 (Florey) possessing pressure sensitive adhesive properties are preferred. Such polyisobutylenes are commercially available under the trademark Vistanex from Exxon as grades LM-MS and LM-MH. One or more thermoplastic elastomers can optionally be included with the pressure sensitive adhesive substances in order to impart the properties of rubber-like extensibility and both rapid and complete recovery from modular strains. Suitable thermoplastic elastomers include medium molecular weight polyisobutylenes having a viscosity average molecular weight of from about 1,150,000 to 1,600,000 (Florey), butyl rubber which is a copolymer of isobutylene with a minor amount of isoprene having a viscosity average molecular weight of from about 300,000 to about 450,000 (Florey), and styrene copolymers such as styrene-butadiene-styrene (S-B-S), styrene-isoprene-styrene (S-I-S), and styrene-ethylene/butylene-styrene (S-EB-S) which are commercially available, for example, from Shell Chemical Co. under the trademark Kraton as Kraton D1100, Kraton D1107, Kraton 4000, Kraton G1600, and Kraton G4600. Preferred thermoplastic elastomers are butyl rubber having a viscosity average molecular weight of about 425,000 (commercially available as grade 077), polyisobutylene having a viscosity average molecular weight of about 1,200,000 (commercially available under the trademark Vistanex from Exxon as grade L-100), and styrene-isoprene-styrene (S-I-S) copolymers (commercially available from Shell as Kraton D 1107).

The pressure sensitive adhesive component including the optional thermoplastic elastomer is present at from about 30% to abput 70% by weight of adhesive layer 11, preferably from about 40% to about 50% by weight. The thermoplastic elastomer can be employed at up to three times the weight of the pressure sensitive elastomeric substances but preferably the thermoplastic elastomer if present will be at from about 20% to about 40% by weight of the pressure sensitive elastomeric substance.

Suitable water soluble hydrocolloids for inclusion in adhesive layer 11 are sodium carboxymethylcellulose pectin, geletin, guar gum, locust bean gum, and gum karaya. These gums impart wet tack, i.e., the ability to adhere to moist surfaces, to adhesive layer 11. One or more water swellable cohesive strengthening agents can optionally be included with the water soluble hydrocolloids in order to control the rate of hydration of water soluble gums. Suitable cohesive strengthening agents include finely divided substantially water insoluble cross-linked sodium carboxymethylcellulose such as that commercially available under the trademark Aqualon or that described in U.S. Pat. No. 3,589,364 and available commercially from the Buckeyl Cellulose Corp., finely divided substantially water insoluble starch-acrylontrile graft copolymer such as that described in U.S. Pat. No. 3,661,815 and commercially available from the Grain Processing Corp., finely divided substantially water insoluble cross-linked dextran such as that commercially available under the trademark Sephadex, finely divided purified wood cellulose such as that commercially available under the trademark Solka-Floc,and finely divided inert natural or synthetic fibrous material such as cotton.

The water soluble hydrocolloids and the optional water swellable or inert cohesive strengthening agents together are present at from about 35% to about 65% by weight of adhesive layer 11, preferably from about 45% to about 60% by weight.

Polymeric film 12 is laminated onto the surface of adhesive layer 11 and is a thin continuous or discontinuous film of polymeric material such as polyethylene, polypropylene, polyurethane, polyvinylchloride, etc. In component A, the adhesive layer 11 will vary in thickness from about 10 to about 120 mils and the film 12 will vary in thickness from about 1 to about 10 mils.

Small amounts, i.e., less than about 10% by weight of the adhesive layer 11, of other ingredients may be included in the adhesive layer 11. For example, a plasticizer such as mineral oil, an antioxidant such as butylated hydroxyanisole, a deodorant or perfume agent may be included. In addition, small amounts of a pharmacologically active ingredient can be included in the adhesive composition. For example, an antibiotic or antimicrobial agent such as neomysin, an antiseptic agent such as povidone iodine, or anti-inflammatory agent such as hydrocortisone or triamcinolone acetonide.

Component A is prepared as follows. A premix is prepared of the water soluble gums, water swellable or inert cohesive strengthening agent and any other optional sustances. The premixed powder is then placed in a heavy duty high shear sigma blade or equivalent type mixer. The viscous pressure sensitive adhesive component is then added in two or three equal segments. Mixing is allowed to proceed for approximately ten minutes between each addition of the viscous material. The resultant dough-like mass is then extruded or rolled or pressed to desired thickness. In working with large batches of material, the dough-like mass may be kneaded prior to the extrusion step. Alternatively, the process may be varied by first working the viscous pressure sensitive adhesive material in the mixer for about ten minutes and then adding the powder premix to two or three equal segments with agitation for about 15 minutes between each addition. When the pressure sensitive adhesive component includes an amount of optional thermoplastic elastomer, such elastomer is first blended by geometric dilution with the pressure sensitive adhesive material in a heated high shear sigma blade or equivalent type mixer. Polymeric film 12 is then laminated onto one side of the adhesive layer and silicone coated release paper on the other to form large slabs or a continuous web of the adhesive laminate. Component A of desired configuration including starter hole 20 are then die cut.

Component B is a coupling element. Preferably, the coupling element (as best shown in FIG. 3) is in the form of a cylindrical rib 22 extending substantially perpendicularly from a flat flange 21 and includes a thin resilient flexible and deflectible seal strip 23. As shown, the seal strip 23 is of tapering form seen in cross-section and extends at an angle radially inwardly from an inner surface of rib 22. Another surface of rib 22 may be provided as shown with peripheral rim 24. Coupling B is formed from any suitable polymeric material such as polyethylene, polypropylene, etc., and is permanently affixed to the surface of polymeric film 12 by heat sealing, ultrasonic welding, by impulse welding, or by use of adhesives. Of course, coupling element B is affixed to film 12 so as to surround starter hole 20.

Component C consists of microporous adhesive layer 31 and a porous backing layer 32. The term microporous is used since the surface of adhesive layer 31 appears to be continuous but when viewed under a microscope the adhesive layer is revealed to be sponge-like having randomly located channels and voids.

The microporous adhesive layer can be of the acrylic type as taught by copeland in U.S. Pat. No. 3,121,021. However, preferably, the adhesive layer 31 is made the same ingredients as adhesive layer 11 with the microporosity resulting from a difference in the manner of processing. Thus, adhesive layer 31 is preferably a homogeneous blend of one or more pressure sensitive viscous or elastomeric materials having intimately dispersed therein one or more water soluble hydrocolloid gums and optionally including one or more thermoplastic elastomers and/or one or more water swellable cohesive strengthening agents. In addition to the various minor optional ingredients such as antioxidants, preservatives, plasticizers, etc., which can be incorporated in either adhesive layer 11 and 31, adhesive layer 31 also can include up to 25% by weight of a tacifier such as terpene resin.

Preferably, adhesive layer 31 includes as the pressure sensitive adhesive and thermoplastic elastomer a mixture of a low molecular weight polyisobutylene (grade LM-MH or LM-MS) and a medium molecular weight polyisobutylene (grade L-100). Such elatomeric materials comprise from about 30% to about 60% by weight of adhesive layer 31, preferably from about 35% to about 50% by weight of adhesive layer 31. The water soluble hydrocolloids and optional water swellable cohesive strengthening agents are present at from about 20% to about 65% by weight of adhesive layer 31, preferably from about 30% to about 60% by weight of adhesive layer 31. Adhesive layer 31 also preferably includes as a plasticizer up to 10% by weight of mineral oil and up to 25% by weight of terpene resin.

The adhesive layer 31 varied from about 1 mil to about 10 mils in thickness and contains holes or pores of from about 10 microns to about 300 microns in size and a porosity of about 1 to about 100 $cc/sec/in^2$ as determined by ASTM D-726-71 method using Gurley Densometer 4110 at 4.89 inches of water $\Delta$ P.

Porous backing layer 32 can be formed of woven or non-woven fabric such as the rayon web described by Copeland in U.S. Pat. No. 3,121,021, an open mesh polymeric substance such as an open mesh polyethylene or polypropylene or a polymeric foam such as polyurethane foam, polyethylene foam, etc., or a non-woven material made from polyester fibers, polypropylene fibers, nylon fibers, composite olefin fibers, or cellulose fibers which are commercially available, for example, the spun laced polyester product Sontara 8003 from DuPont, the spun bonded composite olefin product #1396 from Kimberley Clark, the polyester product Novonette #149-505 or SP126 from Kendall, the nylon product Cerex #368F from Monsanto, etc. These non-woven spun bonded materials are the preferred porous backing layers. The porous backing layer can vary in thickness from about 3 mils to about 20 mils.

Component C is prepared according to the procedure of Copeland when adhesive layer 31 is an acrylic type adhesive. When adhesive layer 31 is a mixture of elastomeric substances and hydrocolloids, then component C is prepared by dispersing the viscous or elastomeric pressure sensitive adhesive materials, thermoplastic elastomers, water soluble hydrocolloids, water swellable cohesive strengthening agents, tackifiers, plasticizers, and other optional ingredients in a hydrocarbon solvent such as toluene, heptane, or hexane or mixtures thereof to form a slurry. The slurry is then deposited, for example, by means of a knife-over-roller, onto a web of silicone coated release paper. The slurry is deposited at a wet thickness of from about 5 mils to about 40 mils, preferably about 10 mils thick. The release paper having the adhesive layer 31 is then passed through a drying tunnel, for example, a multi-zone hot air oven, where it is dried to less than 1% by weight of residual solvent. The air temperature and velocity through the drying zone are controlled so that numerous small bubbles are generated from the solvent evaporation resulting in voids in the adhesive layer which provide the desired microporosity. The dry adhesive layer is then laminated to a web of porous backing material 32 suitably positioned so that the adhesive layer 31 is pressed into intimate contact with the porous backing material 32. Component C of the desired configuration is then die cut from the web. The silicone coated release paper is then stripped off that portion of adhesive layer 31 which overlaps flange 21 of coupling element B and film 12 of component A.

Figure 6:
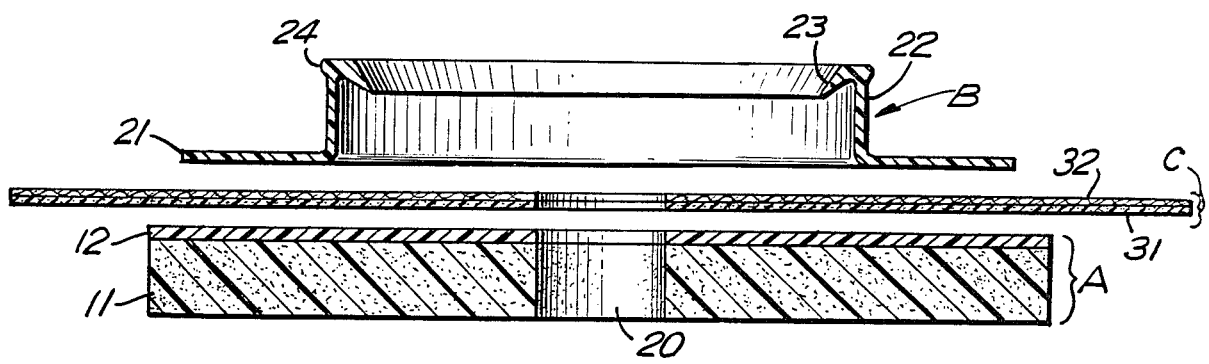
FIG. 6 is an exploded view similar to FIG. 3 of an alternate embodiment of the composite skin barrier of this invention.

An alternate embodiment of the composite skin barrier of this inventiion is shown in FIG. 6. In this embodiment, component C is bonded directly to polymeric film layer 12 of component A. Of course, as in the first embodiment, component C extends beyond the borders of component A so that adhesive layer 31 contacts the skin a distance from the stoma while adhesive layer 11 contacts the skin contiguous with the stoma. Coupling element B is then permanently affixed by impulse heat welding or by use of adhesives directly to porous backing layer 32 so as to encircle the starter hole 20. As shown in FIG. 6, component C may extend across all of polymeric film 12 in which case a starter hole would be included to align with starter hole 20. Alternatively, component C may end directly beneath the area where flange 21 and rib 22 meet so that the skin barrier inside the coupling consists only of component A as in FIG. 1.

Figure 4:
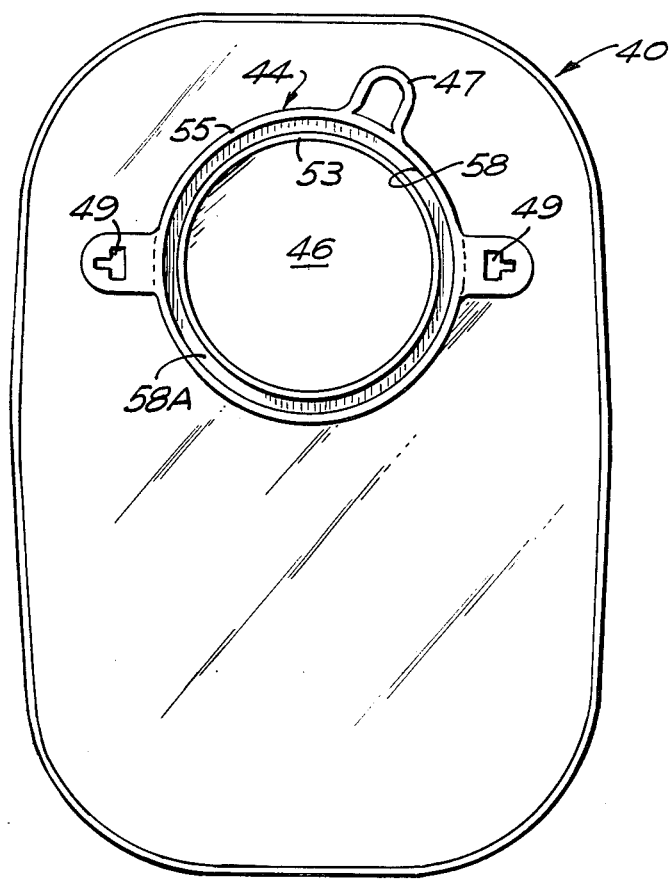
FIG. 4 is a front view of an ostomy pouch having a coupling element enabling it to be affixed to the skin barrier shown in FIGS. 1 to 3.
Figure 5:
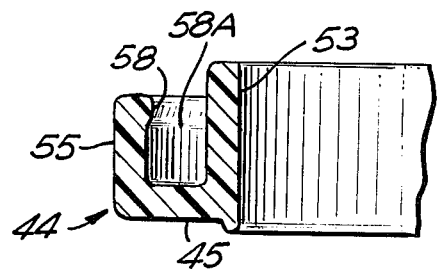
FIG. 5 is an enlarged section taken in a vertical plane of the pouch coupling element.

The composite skin barriers of this invention are used in conjunction with an ostomy pouch having a coupling element designed to mate with coupling element B. As shown in FIGS. 4 and 5, the pouch 40 includes a coupling member 44 of channel-shape seen in any radial cross-section and has a radially inner wall 53 and a radially outer wall 55. A rim 58 extends inwardly around the inner periphery of the wall 55 and, together with the wall 53, defines a restricted annular mouth or entry 58A into which, in use, the rib 22 of coupling member B is pushed to connect the pouch to the skin barrier. Rim 58 cooperates with rib 24 in providing added mechanical security. Of course, the rib 22 is dimensioned to be gripped between the channel walls. Coupling member 44 is sealed to pouch 40 around the stomal opening 46 by heat welding to surface 45. Coupling 44 is preferably of the same polymeric material as coupling B.

FIG. 4 shows pouch 40 as a closed ended pouch of the type employed by most colostomates. Of course, an open ended pouch having a drainable bottom opening as employed by ileostomates or a pouch having a tap valve may also be used in conjunction with the skin barrier of this invention.

Coupling member 44 includes two ear shaped projections having open.ngs 49 for the attachment of a belt and projection 47 which serves as a grip in uncoupling the pouch from the skin barrier.

The exposed surfaces of adhesive layer 31 and adhesive layer 11 may be covered with silicone coated release paper which is removed just prior to use.

While then rib shaped coupling 22 has been shown as component B of the skin barrier and the channel shaped coupling 44 as part of the pouch, it is possible to reverse the coupling elements. Thus, channel shaped coupling member 44 could be affixed at surface 45 to polymeric film 12 or to porous backing layer 32 in the alternate embodiment and rib shaped coupling member 22 can be affixed to the pouch by sealing flange 21 around stomal opening 46. In this case, surface 45 may be extended outwardly to function as a flange which is then overlapped byn adhesive layer 31.

The coupling element B in the skin barrier of this invention has been shown as having a circular shape. However, the rib member 22 could have other configurations provided, of course, that the pouch coupling element corresponds. Also, component A has been shown as having a circular configuration and component C as having a rectangular configuration. Clearly, other geometric configurations could be employed.

Also, while the composite skin barrier of this invention has been described as consisting of three components permanently affixed to one another, it is, of course, possible to market joined components A and B as a single unit and have the ostomate attach component C separately at the time of use.

The following examples are illustrative of the invention.

EXAMPLE 1

A skin barrier was prepared as follows:

Component A

An adhesive mass was prepared consisting of:

| Ingredient | Percent by weight of the adhesive layer |
|---|---|
| Polyisobutylene (Vistanex LM-MH) | 40 |
| Sodium carboxymethylcellulose | 20 |
| Pectin | 20 |
| Gelatin (powder) | 20 |

A premix was prepared by blending 2 kg. of sodium carboxymethylcellulose, 2 kg. of gelatin and 2 kg. of pectin. The blended premix was added to a heavy duty sigma blade type mixer followed by the addition of 4 kg. of polyisobutylene. Mixing was continued until the blend was homogeneous (about 25 minutes).

The resulting dough mass while hot and soft was extruded and flattened to 70 mils. A sheet of polyethylene of 2 mils thickness was laminated onto one side and silicone coated release paper on the other. The resultant mat was die cut into circular shaped wafers of about 2.5 inches in diameter having a center hole of about 0.5 inches in diameter.

Component B

A polyethylene coupling element as shown in FIGS. 1 to 3 was prepared by injection molding. The circular rib 22 has a diameter of about 1.75 inches and a height of about 0.18 inches. The flange was affixed to the polyethylene film of component A by ultrasonic welding.

Component C

A microporous adhesive mass was prepared consisting of:

| Ingredient | Percent by weight of the microporous adhesive layer |
|---|---|
| Polyisobutylene (Vistanex L-100) | 20 |
| Polyisobutylene (Vistanex LM-MH) | 18 |
| Sodium carboxymethylcellulose | 18 |
| Gelatin (powder) | 15 |
| Terpene resin | 20 |
| Mineral oil | 8.5 |
| Butylated hydroxytoluene | 0.5 |

The above solids were dispersed in sufficient heptane to make a slurry containing 40% by weight of solids. The slurry was applied via a knife-over-roller onto silicone coated release paper to a wet thickness of 10 mils. The material was then passed through a multi-zone oven with a residence time of 5-10 minutes so as to reduce the solvent content to less than 1%. The resulting dry adhesive layer was from about 2 to 3 mils thick and had a porosity of about 5 cc/sec/in$^2$. As the dry adhesive film emerged from the oven, it was laminated to a web of spunlaced polyester fiber (DuPont Sontara 8003) coming from a roll suitably positioned so that the adhesive was pressed into intimate contact with the spunlaced material.

The resulting microporous tape was die cut into 4 inch squares having a center hole of about 2 inches. A portion of the silicone coated release paper around the center hole was stripped away and the microporous tape was pressed into contact with flange 21 of the coupling element.

The overall dimensions of components A and C and the diameter of circular rib 22 of component B were varied to obtain skin barriers usable with different size stomas.

EXAMPLES 2-11

Following the procedure of Example 1 but employing the following ingredients in adhesive layer 11 of component A other skin barriers within the scope of this invention are prepared. The ingredients are listed in percent by weight of the adhesive layer.

| Ingredient | 2 | 3 | 4 | 5 | 6 | 7 | 8 | 9 | 10 | 11 |
|---|---|---|---|---|---|---|---|---|---|---|
| Polyisobutylene (Vistanex LM-MH) | 40 | — | 40 | 32 | — | 30 | 50 | 45 | — | 38 |
| Polyisobutylene (Vistanex LM-MS) | — | 45 | — | — | 36 | — | — | — | 45 | — |
| Guar gum | 60 | 25 | 30 | — | — | 25 | 25 | 25 | 25 | 28.5 |
| Locust Bean Gum | — | — | — | — | 25 | — | — | — | — | — |
| Pectin | — | 15 | — | — | — | — | — | 15 | — | 19 |
| Karaya | — | — | — | 20 | — | — | — | — | — | — |
| Gelatin | — | — | — | 20 | — | — | — | — | — | — |
| Sodium carboxymethylcellulose | — | — | 12 | 20 | 20 | 20 | 25 | — | 15 | — |
| Cross-linked sodium carboxymethylcellulose (Aqualon R) | — | — | 18 | — | — | 15 | — | 15 | 15 | — |
| Starch-acrylonitrile graft copolymer (Grain Processing Corp. Polymer 35-A-100) | — | 15 | — | — | — | — | — | — | — | — |
| Cross-linked dextran (Sephadex CM-C50) | — | — | — | — | 10 | — | — | — | — | — |
| Kraton 1107 | — | — | — | — | — | 10 | — | — | — | — |
| Butyl rubber (077) | — | — | — | — | 9 | — | — | — | — | 9.5 |
| Polyisobutylene (Vistanex L-100) | — | — | — | 8 | — | — | — | — | — | — |
| Cotton | — | — | — | — | — | — | — | — | — | 5 |

EXAMPLES 12-19

Following the procedure of Example 1 but employing the following ingredients in microporous adhesive layer 31 of component C other skin barriers within the scope of this invention are prepared. The ingredients are listed in percent by weight of the adhesive layer.

| Ingredient | 12 | 13 | 14 | 15 | 16 | 17 | 18 | 19 |
|---|---|---|---|---|---|---|---|---|
| Polyisobutylene (Vistanex LM-MH) | — | 20 | 25 | — | 20 | — | 25 | — |

-continued

| Ingredient | 12 | 13 | 14 | 15 | 16 | 17 | 18 | 19 |
|---|---|---|---|---|---|---|---|---|
| Polyisobutylene (Vistanex LM-LS) | 20 | — | — | 20 | — | 20 | — | 18 |
| Guar gum | 35 | 20 | — | 20 | — | 20 | 15 | 20 |
| Locust Bean gum | — | — | — | — | 25 | — | — | — |
| Pectin | — | — | 10 | — | — | — | — | — |
| Karaya | — | — | — | 10 | — | — | — | — |
| Gelatin | — | — | 10 | — | — | — | — | — |
| Sodium carboxymethylcellulose | — | — | 10 | 10 | 10 | 10 | 16 | 13 |
| Cross-linked sodium carboxymethylcellulose (Aqualon R) | — | 15 | — | — | 10 | 10 | — | — |
| Starch-acrylonitrile graft copolymer (Grain Processing Corp. Polymer 35-A-100) | — | 18 | — | — | — | — | — | — |
| Cross-linked dextran (Sephadex CM-C50) | — | — | 7 | — | — | — | — | — |
| Terpene resin | 20 | — | 15 | 20 | 15 | 20 | 20 | 20 |
| Mineral Oil | 8.5 | 8.5 | 7.5 | 8.5 | 6.5 | 6.5 | 8.5 | 8.5 |
| Butylated hydroxytoluene | 0.5 | 0.5 | 0.5 | 0.5 | 0.5 | 0.5 | 0.5 | 0.5 |
| Kraton 1107 | — | — | 15 | — | — | 13 | — | — |
| Butyl rubber (077) | — | — | — | 11 | — | — | — | — |
| Polyisobutylene (Vistanex L-100) | 16 | 18 | — | — | 13 | — | 15 | 20 |

What is claimed is:

1. A composite skin barrier for use by ostomates including a first component comprising an adhesive layer and an outer polymeric film said first component having a centrally located stomal opening adapted to fit the skin barrier around a stoma, an intermediate component comprising a microporous adhesive layer and an outer porous backing layer said intermediate component also having a centrally located stomal opening in alignment with the stomal opening in said first component said microporous adhesive layer bonded to and covering at least a portion of the outer polymeric film of said first component and wherein said intermediate component extends beyond the borders of said first component, and a coupling component comprising an outwardly extending flange permanently affixed to said porous backing layer in an area surrounding said stomal opening and a cylindrical rib extending in an upward direction perpendicularly from said flange.

2. A skin barrier according to claim 1 wherein the adhesive layer of said first component comprises a homogeneous blend of one or more pressure sensitive natural or synthetic viscous or elastomeric adhesive substances which can optionally include one or more thermoplastic elastomers and having dispersed therein one or more water soluble hydrocolloid gums which can optionally include one or more water swellable or inert natural or synthetic fibrous cohesive strengthening agents and other optional ingredients selected from the group consisting of anti-oxidants, preservatives, and plasticizers.

3. A skin barrier according to claim 2 wherein the adhesive layer of said first component comprises a homogeneous blend of from about 30% to about 70% by weight of a pressure sensitive substance selected from the group consisting of natural rubber, silicone rubber, acrylonitrile rubber, polyurethane rubber, and low molecular weight polyisobutylene and one or more optional thermoplastic elastomers selected from the group consisting of medium molecular weight polyisobutylene, butyl rubber, and styrene copolymers and having dispersed therein from about 35% to about 65% by weight of one or more water soluble hydrocolloids selected from the group consisting of sodium carboxymethylcellulose, pectin, gelatin, guar gum, locust bean gum, and gum karaya and one or more optional water swellable or inert cohesive strengthening agents selected from the group consisting of cross-linked sodium carboxymethylcellulose, starch-acrylonitrile graft copolymer, cross-linked dextran, purified wood cellulose, and cotton.

4. A skin barrier according to claim 3 wherein the adhesive layer of said first component comprises a homogeneous blend of from about 40% to about 50% by weight of low molecular weight polyisobutylene and one or more optional thermoplastic elastomers selected from the group consisting of medium molecular weight polyisobutylene, butyl rubber, and styrene isoprene copolymers and having dispersed therein from about 45% to about 60% by weight of one or more water soluble hydrocolloids selected from the group consisting of sodium carboxymethylcellulose, pectin, gelatin, guar gum, locust bean gum, and gum karaya and one or more water swellable or inert cohesive strengthening agents selected from the group consisting of cross-linked sodium carboxymethylcellulose, starch-acrylonitrile graft copolymer, cross-linked dextran, purified wood cellulose, and cotton.

5. A skin barrier according to claim 4 wherein said first component comprises an adhesive layer consisting of a blend of about 40% by weight of polyisobutylene, about 20% by weight of sodium carboxymethylcellulose, about 20% by weight of pectin, and about 20% by weight gelatin and said polymeric film is polyethylene.

6. A skin barrier according to claim 1 wherein said intermediate component microporous adhesive layer has a porosity of from about 1 to 100 cc/sec/in$^2$ and comprises a homogeneous blend of one or more pressure sensitive natural or synthetic viscous or elastomeric adhesive substances which can optionally include one or more thermoplastic elastomers and having dispersed therein one or more water soluble hydrocolloid gums which can optionally include one or more water swellable cohesive strengthening agents and other optional ingredients selected from the group consisting of antioxidants, preservatives, plasticizers, and tackifiers and said intermediate component porous backing layer comprises woven or non-woven fabric, an open mesh polymeric substance, a polymeric foam, or a non-woven material made from polyester fibers, polypropylene fibers, nylon fibers, composite olefin fibers, or cellulose fibers.

7. A skin barrier according to claim 6 wherein the microporous adhesive layer of said intermediate component comprises a homogeneous blend of from about 30% to about 60% by weight of a pressure sensitive adhesive substance selected from the group consisting of natural rubber, silicone rubber, acrylonitrile rubber, polyurethane rubber, and low molecular weight polyisobutylene and one or more optional thermoplastic elastomers selected from the group consisting of medium molecular weight polyisobutylene, butyl rubber, and styrene copolymers, from about 20% to about 65% by weight of one or more water soluble hydrocolloids selected from the group consisting of sodium carboxymethylcellulose, pectin, gelatin, guar gum, locust bean gum, and gum karaya and one or more optional water swellable cohesive strengthening agents selected from the group consisting of cross-linked sodium carboxymethylcellulose, starch-acrylonitrile graft copolymers, and cross-linked dextran, up to 10% by weight of mineral oil, and up to 25% by weight of terpene resin.

8. A skin barrier according to claim 7 wherein the microporous adhesive layer of said intermediate component comprises a homogeneous blend of from about 35% to about 50% by weight of a blend of low molecular weight and medium molecular weight polyisobutylenes having dispersed therein from about 30% to about 60% by weight of one or more water soluble hydrocolloids selected from the group consisting of sodium carboxymethylcellulose, pectin, gelatin, guar gum, locust bean gum, and gum karaya and one or more optional water swellable cohesive strengthening agents selected from the group consisting of cross-linked sodium carboxymethylcellulose, starch-acrylonitrile graft copolymer, and cross-linked dextran, up to 10% by weight of mineral oil, and up to 25% by weight of terpene resin.

9. A skin barrier according to claim 8 wherein said intermediate component comprises a microporous adhesive layer consisting of a blend of about 18% by weight of low molecular weight polyisobutylene, about 20% by weight of medium molecular weight polyisobutylene, about 18% by weight of sodium carboxymethylcellulose, about 15% by weight of gelatin, about 20% by weight of terpene resin, about 8.5% by weight of mineral oil, and about 0.5% by weight of butylated hydroxytoluene and said porous backing is spun bonded polyester fiber.

* * * * *